(12) United States Patent
Friedman et al.

(10) Patent No.: US 12,042,206 B2
(45) Date of Patent: *Jul. 23, 2024

(54) DEVICES AND METHODS FOR TREATMENT OF SKIN CONDITIONS

(71) Applicant: Drexel University, Philadelphia, PA (US)

(72) Inventors: Peter C Friedman, New City, NY (US); Vandana Miller, Philadelphia, PA (US); Gregory Fridman, Philadelphia, PA (US); Abraham Lin, Philadelphia, PA (US); Alexander Fridman, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/157,671

(22) Filed: Jan. 20, 2023

(65) Prior Publication Data

US 2023/0371998 A1 Nov. 23, 2023

Related U.S. Application Data

(63) Continuation of application No. 16/321,686, filed as application No. PCT/US2017/044791 on Aug. 1, 2017, now Pat. No. 11,571,249.

(Continued)

(51) Int. Cl.
*A61B 18/04* (2006.01)
*A61B 18/00* (2006.01)

(Continued)

(52) U.S. Cl.
CPC .............. *A61B 18/042* (2013.01); *A61N 1/44* (2013.01); *H05H 1/2406* (2013.01); *A61B 2018/00452* (2013.01)

(58) Field of Classification Search
None
See application file for complete search history.

(56) References Cited

U.S. PATENT DOCUMENTS 5,586,981 A * 12/1996 Hu ........................ A61B 18/203
606/9
7,094,322 B1 * 8/2006 Kovach ................ H05H 1/2406
315/111.21

(Continued)

FOREIGN PATENT DOCUMENTS

CN 101175493 A 5/2008
CN 101854874 A 10/2010

(Continued)

OTHER PUBLICATIONS

Fridman et al., "Applied Plasma Medicine", Plasma Processes and Polymers, 2008, 5, 503-533.

(Continued)

*Primary Examiner* — Srinivas Sathiraju
(74) *Attorney, Agent, or Firm* — BakerHostetler

(57) ABSTRACT

Disclosed is a method for treating actinic keratosis of tissue of a patient, the method including contacting non-thermal, atmospheric pressure plasma over areas of the tissue having actinic keratosis for a time and at treatment conditions effective to give rise to an at least partial amelioration of the keratosis.

20 Claims, 3 Drawing Sheets

Related U.S. Application Data

(60) Provisional application No. 62/369,491, filed on Aug. 1, 2016.

(51) Int. Cl.
*A61N 1/44* (2006.01)
*H05H 1/24* (2006.01)

(56) References Cited

U.S. PATENT DOCUMENTS

| | | | |
|---|---|---|---|
| 8,267,884 B1* | 9/2012 | Hicks | A61B 18/042 604/23 |
| 8,388,618 B2 | 3/2013 | Fridman et al. | |
| 8,521,274 B2 | 8/2013 | Gutsol et al. | |
| 8,725,248 B2 | 5/2014 | Gutsol et al. | |
| 8,896,211 B2* | 11/2014 | Ish-Yamini Tomer | B09C 1/00 604/23 |
| 9,226,790 B2* | 1/2016 | Zemel | A61B 18/042 |
| 9,757,196 B2* | 9/2017 | Moss | A61B 18/1815 |
| 11,571,249 B2* | 2/2023 | Friedman | A61N 1/44 |
| 2004/0147501 A1* | 7/2004 | Dolmans | A61K 31/555 604/20 |
| 2004/0171601 A1* | 9/2004 | Fukumura | A61K 41/0076 604/20 |
| 2004/0176737 A1* | 9/2004 | Henley | A61N 1/30 604/20 |
| 2004/0236267 A1* | 11/2004 | Pierce | A61N 5/06 604/20 |
| 2004/0258850 A1* | 12/2004 | Straccia | B05D 7/144 427/532 |
| 2005/0182351 A1* | 8/2005 | Henley | A61N 1/30 604/20 |
| 2005/0274122 A1* | 12/2005 | Chang | H05H 1/24 62/5 |
| 2006/0052739 A1* | 3/2006 | Henley | A61N 1/30 604/20 |
| 2006/0105974 A1* | 5/2006 | Lange | C12N 15/1138 604/20 |
| 2007/0078434 A1* | 4/2007 | Keusch | A61N 1/0448 604/20 |
| 2007/0184201 A1* | 8/2007 | Holubka | B05D 3/063 427/407.1 |
| 2010/0125267 A1* | 5/2010 | Lee | A61B 18/042 315/111.21 |
| 2013/0041443 A1 | 2/2013 | Weissberg et al. | |
| 2013/0071286 A1* | 3/2013 | Watson | A61M 16/06 315/111.21 |
| 2013/0072858 A1* | 3/2013 | Watson | A61M 15/02 604/23 |
| 2013/0072860 A1* | 3/2013 | Watson | A61N 1/44 604/23 |
| 2013/0345620 A1* | 12/2013 | Zemel | H05H 1/2418 604/24 |
| 2014/0361689 A1* | 12/2014 | Weisgerber | H01J 37/32229 315/111.21 |
| 2015/0105716 A1* | 4/2015 | Ish-Yamini Tomer | A61N 1/44 29/25.35 |
| 2015/0151135 A1 | 6/2015 | Kalghatgi et al. | |
| 2015/0221476 A1* | 8/2015 | Watson | A61L 2/14 315/111.21 |
| 2016/0023183 A1* | 1/2016 | Levin | B01J 19/088 422/186.04 |
| 2016/0089545 A1 | 3/2016 | Juluri et al. | |
| 2016/0113701 A1* | 4/2016 | Zemel | A61B 18/042 604/23 |
| 2016/0307735 A1* | 10/2016 | Konesky | A61L 2/0011 |
| 2017/0032944 A1* | 2/2017 | Jacofsky | H01J 37/32082 |
| 2017/0304601 A1* | 10/2017 | Gardner | A61N 1/327 |
| 2018/0177550 A1* | 6/2018 | Anderson | A61B 18/203 |
| 2019/0321091 A1* | 10/2019 | Zemel | A61B 18/042 |
| 2020/0038530 A1* | 2/2020 | Yildirim | A61H 7/005 |
| 2020/0254008 A1* | 8/2020 | Kim | A61K 33/00 |
| 2021/0023250 A1* | 1/2021 | Golkowski | A61L 2/26 |
| 2021/0260395 A1* | 8/2021 | Friedman | A61N 1/44 |
| 2021/0282831 A1* | 9/2021 | Friedman | A61N 1/44 |

FOREIGN PATENT DOCUMENTS

| | | | |
|---|---|---|---|
| CN | 102348479 A | 2/2012 | |
| CN | 104810930 A | 7/2015 | |
| CN | 105578158 A | 5/2016 | |
| EP | 3132809 A1 | 2/2017 | |
| EP | 3132809 A1 * | 2/2017 | A61K 35/12 |
| EP | 3490476 A1 | 6/2019 | |
| GB | 2496879 A | 5/2013 | |
| GB | 2496879 A * | 5/2013 | A61L 2/0011 |
| WO | 2006/077582 A2 | 7/2006 | |
| WO | 2008/093319 A2 | 8/2008 | |
| WO | 2009/055764 A1 | 4/2009 | |
| WO | 2010/078581 A1 | 7/2010 | |
| WO | 2016/048689 A1 | 3/2016 | |
| WO | 2016/094890 A1 | 6/2016 | |
| WO | 2018/026750 A1 | 2/2018 | |
| WO | WO-2018026750 A1 * | 2/2018 | A61B 18/042 |
| WO | 2018/069549 A1 | 4/2018 | |
| WO | WO-2018069549 A1 * | 4/2018 | A61B 18/0218 |

OTHER PUBLICATIONS

Fridman et al., "Blood coagulation and living tissue sterilization by floating-electrode dielectric barrier discharge in air", Plasma Chemistry and Plasma Processing, 2006, 26, 425-442.

Lin et al., "Uniform Nanosecond Pulsed Dielectric Barrier Discharge Plasma Enhances Anti-Tumor Effects by Induction of Immunogenic Cell Death in Tumors and Stimulation of Macrophages", Plasma Processes and Polymers, 2015, 12, 1392-1399.

Miller et al., "Plasma Stimulation of Migration of Macrophages", Plasma Processes and Polymers, 2014, 11, 1193-1197.

Miller et al., "Why Target Immune Cells for Plasma Treatment of Cancer", Plasma Chemistry and Plasma Processing, 2016, 36, 259-268.

* cited by examiner

DEVICES AND METHODS FOR TREATMENT OF SKIN CONDITIONS

CROSS-REFERENCE TO RELATED APPLICATIONS

This application is a continuation of now-allowed U.S. patent application Ser. No. 16/321,686 filed Jan. 29, 2019, which is the National Stage Application of International Patent Application No. PCT/US2017/044791 filed Aug. 1, 2017, which claims priority to and the benefit of U.S. Patent Application No. 62/369,491, filed Aug. 1, 2016, the entireties of which foregoing applications are incorporated herein for any and all purposes.

TECHNICAL FIELD

This disclosure relates to treating skin conditions. Particularly, the disclosure relates to using plasma to treat pre-cancerous conditions, neoplastic, hyperproliferative, and inflammatory conditions of the skin.

BACKGROUND

Skin conditions and diseases are prevalent and are often difficult to treat. If left untreated, they may progress to more serious conditions and may lead to more severe consequences, such as permanent scarring or various cancers. The treatment of actinic keratoses (AKs), for example, represents a daily challenge for dermatologists: the available modalities all have significant downsides, such as pain, inflammation, treatment site reaction, incomplete response and frequent recurrences. The present invention is intended to address some of these issues.

SUMMARY

Disclosed are methods and devices for treating specific skin conditions with plasma. According to one embodiment, a method for treating actinic keratosis of tissue of a patient includes guiding non-thermal, atmospheric pressure plasma over areas of the tissue having actinic keratosis for a length of time effective to give rise to an at least partial amelioration of the keratosis. The plasma may be generated by a plasma generation device having a high-voltage electrode and an insulating or a semiconducting barrier. The duration of time of exposure of the plasma is sufficient to result in fewer or lesser visible or palpable keratosis lesions as a result of treatment.

According to another embodiment, a device for treating actinic keratosis of tissue of a patient includes a high voltage electrode, an insulating or semiconducting barrier, a power source capable of providing a voltage, and a pulse generator. The device generates a non-thermal plasma. In some embodiments, the insulating or semiconducting barrier may comprise a ceramic, organic or inorganic polymer, glass, or other carbide, nitride, or oxide insulators, including quartz. The power source may provide power in a range of about 10 kV to about 60 kV, for example 20 kV. The pulse generator may operate to provide one or more pulses at about 50 to 3,500 Hz, for example 200 Hz, each pulse lasting in a range of from about 1 to 500 ns, for example about 10-20 ns.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. Furthermore, the drawings are not necessarily drawn to scale. In the drawings.

DETAILED DESCRIPTION OF ILLUSTRATIVE EMBODIMENTS

Figure 1:
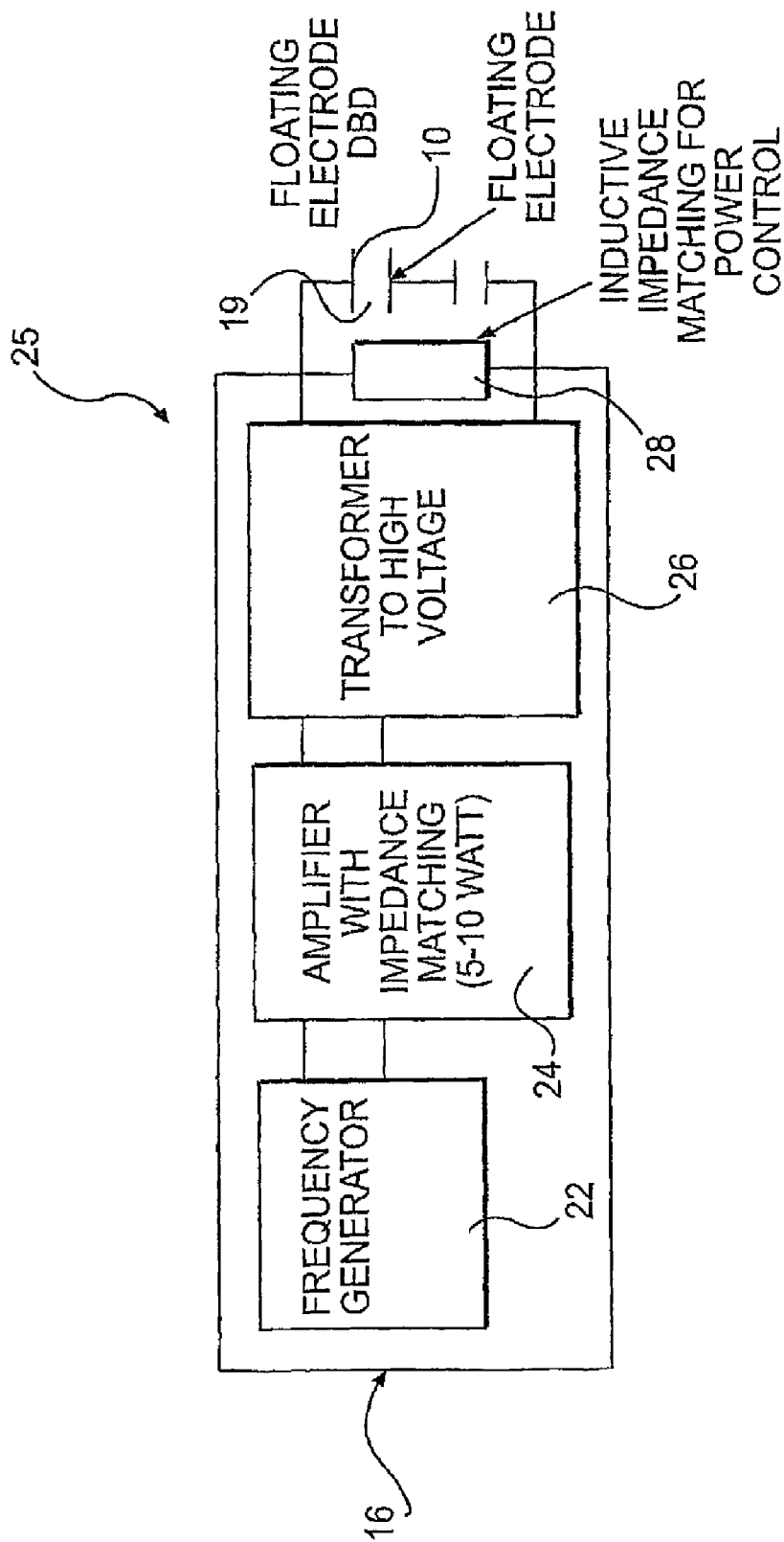
FIG. 1 illustrates an exemplary electrical diagram of a non-thermal plasma and a power supply according to an embodiment.

Aspects of the disclosure will now be described in detail with reference to the drawings, wherein like reference numbers refer to like elements throughout, unless specified otherwise. Certain terminology is used in the following description for convenience only and is not limiting.

The term "plurality," as used herein, means more than one. The singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of."

When values are expressed as approximations by use of the antecedent "about," it will be understood that the particular value forms another embodiment. In general, use of the term "about" indicates approximations that can vary depending on the desired properties sought to be obtained by the disclosed subject matter and is to be interpreted in the specific context in which it is used, based on its function, and the person skilled in the art will be able to interpret it as such. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, reference to values stated in ranges includes each and every value within that range.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Throughout this specification, words are to be afforded their normal meaning as would be understood by those skilled in the relevant art. However, so as to avoid misunderstanding, the meanings of certain terms will be specifically defined or clarified.

Actinic keratosis often appears as a crusty, scaly growth caused by damage from exposure to ultraviolet (UV) radiation. It is considered a precancer, and if left untreated, it could develop into a skin cancer, for example squamous cell carcinoma. Actinic keratoses typically occur on the face, lips, ears, bald scalp, shoulders, neck and back of the hands and forearms. They may range in size from a tiny spot to as much as an inch in diameter.

Electrical discharge plasma has a very strong influence on living tissue. This strong influence can be of two kinds: thermal and non-thermal. Thermal influence of plasma that results in rapid heating of living tissue is well studied and is used for, for example, cauterization. In other cases the thermal influence of plasma results in living tissue desiccation and burns and thus is undesirable. The non-thermal influence of electrical discharge plasma, caused by active plasma particles (electrons, ions, radicals, and other chemically active species) and UV radiation, may be useful in many cases, for example, for living tissue disinfection and sterilization, for skin disease treatment, for blood coagulation, etc. The closer to the living tissue the active plasma is located and the higher is electrical field in the plasma, the higher the intensity and efficacy of the non-thermal plasma treatment. Available methods of non-thermal plasma treatment are relatively weak and are effected usually by plasma jet or afterglow treatment because there are limitations on the power flux to the living tissue (to prevent overheating of the tissue) and on the total current and current density which may flow through the living tissue (to prevent damage of the tissue and nerve channels). Since the power of electrical discharge that creates plasma is a product of the discharge current and voltage, the higher the voltage—the lower the current, when power is fixed.

Thermal plasma devices that do not rely on delivery of current into tissue have also been developed for coagulation and cauterization of tissue. Instead, the plasma is employed to rapidly heat a gas. The heated gas (often argon due to its inert properties) is subsequently directed toward the tissue in the form of a jet whereby the heated gas transfers its thermal energy to the tissue. The effect of such plasma treatment is mostly thermal because many of the active chemical species in the remotely created plasma are short-lived and do not survive transport of the heated gas flow to the tissue.

Disclosed herein are devices and methods for treating skin conditions using non-thermal plasma. A method for treating actinic keratosis of tissue of a patient may include applying plasma to a tissue having one or more actinic keratoses. The plasma may be held in position to contact the actinic keratosis for an extended duration, ranging for example, from 10 seconds to 60 seconds, from 1 minute to 5 minutes, from 5 minutes to 10 minutes, or from 10 minutes to 30 minutes, or a range defined by two or more of these ranges. In some embodiments, multiple treatments may be employed, for example 1, 2, 3, 4, 5, or more times. In some embodiments, the plasma may be moved along the surface of the tissue such that the plasma maintains contact with the tissue. Treatment may result in complete or partial amelioration of the treated actinic keratosis, for example the disappearance or the decrease in the number, size, or appearance of visible or palpable lesions. These changes typically appear days, weeks, or months after treatment(s).

The method of exposing the tissue to the plasma may differ in various implementations. In some embodiments, the plasma generation device may be kept in a stationary position such that plasma contacts one or more lesions for the desired duration. Alternatively, the plasma generation device may be moved over the treatment area.

For treatment to be most effective, plasma has to contact the afflicted tissue. The distance between the plasma generation device and the tissue may vary. In some embodiments, the plasma generation device may contact the surface to be treated such that the powered electrode contacts the tissue. In another embodiment, the plasma generation device may be positioned up to about 20 mm away from the treatment surface. In another embodiment, the plasma generation device may be positioned up to about 10 mm away from the treatment surface. In a further embodiment, the plasma generation device may be positioned up to about 5 mm from the treatment surface. In a further embodiment, the plasma generation device may be positioned up to about 1 mm from the treatment surface. In other embodiments, the electrodes may actually be touching the treatment surface.

The plasma may include non-thermal plasma generated at atmospheric pressure. The plasma may be generated by a plasma generation device. In some embodiments, the plasma generation device may have a high-voltage electrode and an insulating or semiconducting barrier. The high-voltage discharge generated may be a Dielectric Barrier Discharge (hereinafter "DBD") created at standard atmospheric conditions and not requiring or creating high temperatures at the treatment location. For example, during DBD treatment, the typical temperature rise is only a few degrees above room temperature during the duration of the treatment.

The DBD is an alternating voltage discharge between two electrodes, at least one of which is typically covered by an insulating dielectric. DBD plasma can be formed in the gas filled area, otherwise known as the discharge gap, between one electrode and a dielectric or between two dielectrics. The DBD is driven by an applied alternating high voltage (typically several kilovolts), which generates a high electric field between the electrodes. In the absence of a dielectric, the discharge starting from the first spark, would rapidly progress to a low-voltage arc discharge, as the electrons in the spark would initiate a series of ionization events, leading to very high current and ultimately to arc formation. The dielectric prevents arc formation by accumulating charge on the surface and generating an electric field that opposes the applied field, thereby limiting the current and preventing uncontrolled discharge development. Alternation of high voltage polarities ensures formation of this discharge in each half of the voltage cycle. Typically, DBD operates in the kilohertz range, including tens or hundreds of kilohertz range, so plasma between the electrodes does not have enough time to extinguish completely, and the discharge looks like a continuous glow and/or stationary or moving filaments in the discharge gap.

In some embodiments, the power source provides power in a range of from about 5 kV to 10 kV, from 10 kV to 20 kV, from 20 kV to 30 kV, from 30 kV to 40 kV, from 40 kV to 50 kV, or in a range comprising two or more of these ranges. In preferred embodiments, the power source provides power of about 20 kV to the electrode.

In some embodiments, the pulse generator provides a series of pulses in a range of from 50 Hz to 100 Hz, from 100 Hz to 200 Hz, from 200 Hz to 300 Hz, from 300 Hz to 400 Hz, from 400 Hz to 500 Hz, from 500 Hz to 1000 Hz, from 1000 Hz to 2000 Hz, from 2000 Hz to 3000 Hz, from 3000 Hz to 4000 Hz, or a range defined by two or more of these ranges, preferably about 200 Hz.

In some embodiments, the pulse generator provides a series of pulses, each pulse having a duration in a range of about 10 ps to 100 ps, from 100 ps to 1 ns, from 1 ns to 5 ns, from 5 ns to 10 ns, from 10 ns to 20 ns, from 20 ns to 30 ns, from 30 ns to 40 ns, from 40 ns to 50 ns, from 50 ns to 60 ns, from 60 ns to 80 ns, from 80 ns to 100 ns, from 100 ns to 200 ns, from 200 ns to 300 ns, from 300 ns to 400 ns, from 400 ns to 500 ns, or a range defined by two or more of these ranges, preferably about 20 ns, and in some embodiments, preferably about 2 ns.

DBD is a typical discharge for non-thermal or cold plasma generation. In thermal plasmas, the temperatures of all plasma components (electrons, ions, gas molecules and atoms) are similar. Plasma can exist for some time if the plasma components are in dynamic equilibrium: recombination of electrons and ions should be balanced by ionization. To provide significant ionization, it is necessary to have energetic particles, usually electrons, with energies of several electron-volts (eV). The average energy of gas particles equals about 1 eV and corresponds to the gas temperature of 11,600 K. This means that more or less stable thermal plasmas always have temperatures above 3500 K or above 5000 K.

In non-thermal plasmas, temperatures of components can be very different and do not have to be in equilibrium. Usually, the temperature of electrons is much higher (more than 10,000 K) than the temperature of heavy particles, such as ions and gas molecules. Typically, low-temperature plasma exists in luminescent lamps. Gas temperatures of the non-equilibrium plasma can be very different and may range from room or ambient temperature to several thousand degrees Kelvin. Plasma is considered to be non-thermal when its gas temperature is not considerably higher than the surrounding temperature, which surrounding temperature may be, for example, room temperature (e.g. 20-25° C.). For the purposes of this disclosure, non-thermal plasma can be characterized by an average plasma gas temperature that does not exceed about 400 K. The plasma electron and ion density may be about $10^{11}$ cm$^{-3}$ to about $10^{13}$ cm$^{-3}$, and, more preferably, above $10^{12}$ cm$^{-3}$. Electron density in DBD filaments, for example, may be about $10^{13}$ cm$^{-3}$ and electron temperatures can range from 10,000 to 30,000 K.

In one apparatus according to the disclosure, the non-thermal plasma discharge may be generated by a high frequency pulsing of high voltage of from about 0.0001 to about 20,000 kHz, optionally, from about 10 to about 30 kHz, using a voltage of about 2 to about 50 kV, optionally, from about 10 to about 30 kV. Whereas the DBD is created by applying a high frequency voltage between two electrodes, the non-thermal plasma discharge used in this invention occurs in a highly localized region between an insulated electrode and a second electrode. The second electrode may be a nearby object, and, in many applications of the present disclosure, the second electrode is a human or animal body. Such non-thermal plasma devices seen as useful in the present methods are described in U.S. Pat. No. 8,725,248, the entirety of which is incorporated by reference for any and all purposes, and at least with respect to structure and operation of non-thermal plasma generation devices.

FIG. 1 shows an electric diagram of an apparatus which employs a human or animal body acts as a floating electrode. The floating electrode may be the afflicted tissue to be treated. Plasma device 25 includes an apparatus for control of the size of plasma gap 19, as well as use of different sizes and shapes of electrodes. The plasma gap is typically from about 0.5-5 mm, but in some cases may be smaller, including down to zero. The electrode may contact the tissue to be treated. The electrodes for treatment of the human or animal body typically have surface areas of about 0.1-10 cm$^2$. The variations in electrode size and shape permit finer control of the size and shape of the treatment area, allowing the operator to customize the treatment. This may be advantageous since it avoids unnecessary plasma treatment of healthy tissue surrounding the treatment area.

Power supply 15 may include a frequency generator 22 and an amplifier 24 to provide, for example, impedance matching of 5-10 watts. Also included are a transformer 26 and apparatus for inductive impedance matching 28 for power control. Power supply 15 for plasma device 25 offers the ability to fine tune the power used in providing the non-thermal plasma to enable fine control of the plasma application. Power supply 15 can be integrated as a single unit. The power supply 15 provides generation of pulsed high voltage with necessary power.

The high-voltage electrical discharge plasma may contact tissue by positioning an insulator or semiconductor between an electrode and tissue which limits the total current and current density through the plasma into the tissue. An apparatus for generating such a plasma discharge can be easily employed by a human operator, or by a remotely controlled machine, and is also suitable for telemedicine. In some embodiments, the plasma generated by the devices described herein may contact the tissue afflicted by one or more medical conditions.

Figure 2:
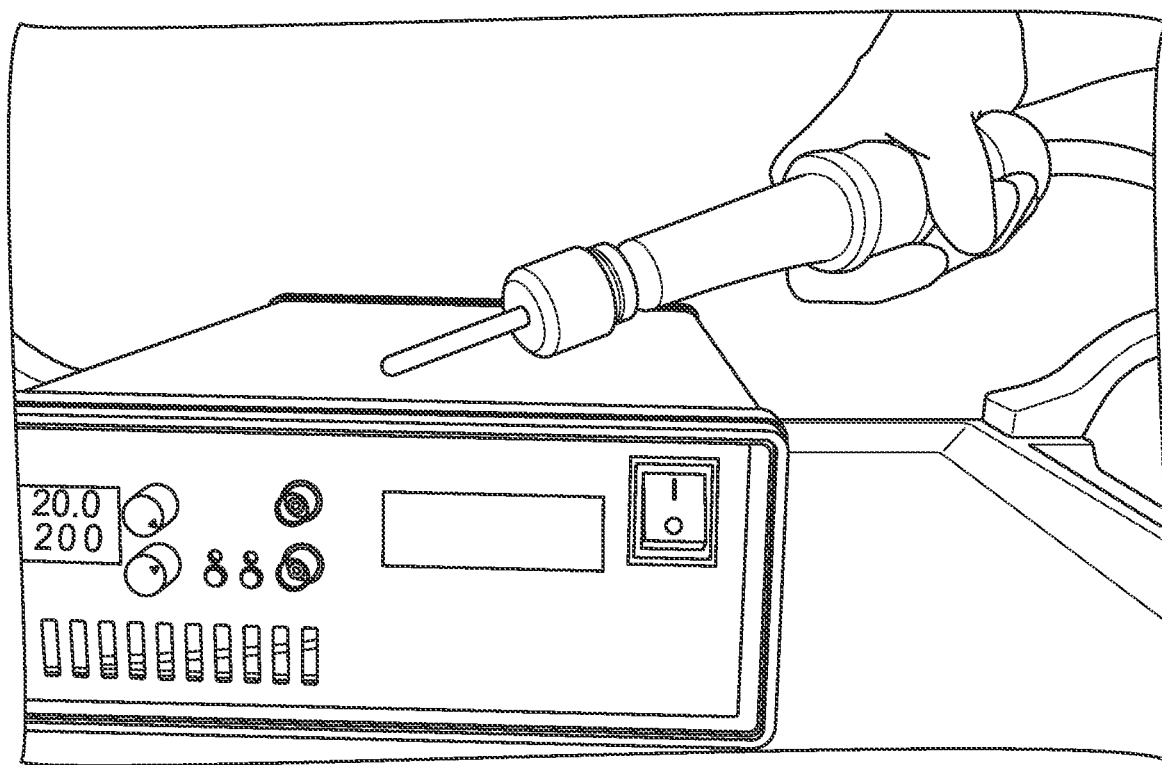
FIG. 2 illustrates an exemplary non-thermal atmospheric pressure plasma device with a hand held electrode according to an embodiment.

The plasma may be generated by a handheld plasma generation device as shown in FIG. 2, the device being configured as described throughout this disclosure. In some embodiments, the generated plasma is used to treat actinic keratosis on human skin tissue.

While the body of this specification has been written solely in terms of actinic keratosis, in other aspects, analogous treatments may be applied to treat additional ailments, such as, but not limited to, keratinocyte carcinoma, squamous cell carcinoma, basal cell carcinoma, Paget's disease, extramammary Paget's disease, melanocyte neoplasm, in situ melanoma, invasive melanoma, lentigo maligna, lentigo maligna melanoma, cutaneous lymphoma, and any other neoplastic, hyper-proliferative, or inflammatory conditions that originate from or are localized to the skin.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein. Accordingly, the descriptions provided here should not be construed to limit the disclosure, and the reader is advised to look to the nature of the claims as a broader description.

Studies have been conducted using the above-disclosed methods and devices to treat actinic keratosis. Experimental trials were directed to studying the utility of uniform non-equilibrium, non-thermal atmospheric pressure plasma ("NTAP") in the treatment of actinic keratoses. NTAP has been shown to selectively induce apoptosis in cancer cell lines in vitro, including squamous cell carcinoma cells. Studies have also suggested that NTAP may additionally upregulate local, as well as tumor-specific, systemic immune response. This may lead to an immunological advantage against actinic keratoses.

A single treatment was conducted, as well as short term follow-up and a case series trial. In this treatment, five patients were enrolled after obtaining informed consent. Three of those patients had biopsy-proven actinic keratoses, and two patients were clinically diagnosed with actinic keratoses. The treatment protocol called for a single treatment using an NTAP device as described throughout this disclosure on the target lesions. One month after treatment, the results were evaluated clinically. Results were additionally analyzed by comparing pretreatment photographs with photographs post-treatment.

Different gradations of the resulting outcome were considered. The outcome was categorized as "fully resolved" if no visible or palpable lesions remained with the exception of minimal site erythema. The amelioration results were categorized as "significantly improved" if there was at least 50% improvement of the lesion (color, size, etc.), as assessed by a clinical practitioner. Gradations of "minor" or "no improvement" were assigned if the improvement was less than 50% in the clinician's assessment based both on examination and on photograph comparison.

A specific plasma generation apparatus was used in this experimental treatment. A pulse generator supplying 20 kV pulses of 20 ns pulse width at 200 Hz was used. These methods are more specifically described in Fridman, G., Peddinghaus, M., Balasubramanian, M., et al., *Blood coagulation and living tissue sterilization by floating-electrode dielectric barrier discharge in air*, Plasma Chemistry and Plasma Processing, 2006; 26:425-442, which is incorporated in its entirety for any and all purposes, and specifically for its description of parameters used in the experimental study described herein.

In other embodiments, the pulse generator can supply pulses in a range of 5 to 25 kV. In other embodiments, the pulse generator can supply pulses having 100 ps to 500 ns pulse widths or 10 ns to 50 ns pulse widths. In still other embodiments, the pulse generator can supply pulses having frequencies 50 to 500 Hz. In another embodiment, the pulse generator may supply pulses having a frequency of about 400 Hz.

The pulse generator supplied energy to a 5 mm diameter quartz-covered copper electrode having a length of 10 cm length and a thickness of 1 mm. The specific device used was from FID GmbH, Germany, www.fidtechnology.com. It will be understood that other plasma generation devices as described throughout this specification may be used, and that this disclosure is not limited to the specific device used in this trial.

The selected parameters of the plasma generation device were chosen for this experimental study to provide sufficient treatment dose at the high level of plasma uniformity required to avoid any tissue damage. The lesions were treated for approximately 1-2 minutes each. Treatment was conducted by gently moving the electrode over the treatment area. Nanosecond pulsed regimes may be advantageous over alternative treatments because they allow for more controlled delivery of plasma to induce stress mediated pathways. This may allow even precancerous cells to be selectively more susceptible to the treatment than other or normal cells.

Figure 3:
FIG. 3 illustrates a condition of skin before treatment (top panel) and condition of the skin one month after treatment (bottom panel) according to an embodiment.

In total, 17 lesions were treated. Nine of the treated lesions showed full clinical resolution one month after the treatment. Three lesions significantly improved. Five lesions showed minor or no improvement. None of the patients in this study experienced any adverse effects related to the treatment. There were no complaints of immediate or delayed treatment site reactions. Referring to FIG. 3, the top panel shows a sample of skin afflicted by actinic keratoses prior to treatment. The bottom panel of FIG. 3 shows the same sample of skin as it appeared one month after treatment.

These results demonstrate that NTAP may serve as an effective, well-tolerated treatment for actinic keratosis. Additional trials involving different treatment settings, treatment frequencies, and longer follow-up periods are being conducted as well. The efficacy numbers of this experimental study are comparable to the reported numbers of other, currently widely-used modalities. NTAP may be an advantageous alternative for existing treatments of actinic keratosis due to the high tolerability and high efficacy.

While the disclosure has been described in connection with the various embodiments of the various figures, it will be appreciated by those skilled in the art that changes could be made to the embodiments described above without departing from the broad inventive concept thereof. It is understood, therefore, that this disclosure is not limited to the particular embodiments disclosed, and it is intended to cover modifications within the spirit and scope of the present disclosure as defined by the claims.

Features of the disclosure that are described above in the context of separate embodiments may be provided in combination in a single embodiment. Conversely, various features of the disclosure that are described in the context of a single embodiment may also be provided separately or in any sub-combination. Finally, while an embodiment may be described as part of a series of steps or part of a more general structure, each said step may also be considered an independent embodiment in itself, combinable with others.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

As those skilled in the art will appreciate, numerous modifications and variations of the present invention are possible in light of these teachings, and all such are contemplated hereby. All references cited within this specification are incorporated by reference in their entireties for all purposes, or at least for their teachings in the context of their recitation.

The invention claimed is:

1. A method for treating actinic keratosis of tissue of a patient, comprising:
    applying a non-thermal, atmospheric pressure plasma over areas of the tissue having actinic keratosis for a length of time effective to give rise to an at least partial amelioration of the keratosis,
    the non-thermal, atmospheric pressure plasma being generated by a device, the device comprising:
    a high voltage electrode, an insulating or semiconducting barrier, a power source capable of providing a voltage, and a pulse generator;
    wherein the device optionally comprises an apparatus for inductive impedance matching, an apparatus for controlling the size of a plasma gap of the device, or both.

2. The method of claim 1, wherein the device further comprises a frequency generator.

3. The method of claim 1, wherein the device is configured to contact the tissue of the patient.

4. The method of claim 1, wherein the device is configured to apply the non-thermal atmospheric plasma at a distance from the tissue of the patient.

5. The method of claim 1, wherein the non-thermal plasma has an average gas temperature that does not exceed about 400 K.

6. The method of claim 1, wherein the insulating or semiconducting barrier comprises a ceramic, organic or inorganic polymer, glass, or other carbide, nitride, or oxide insulator.

7. The method of claim 1, wherein the power source provides power in the range of from about 10 kV to about 60 kV.

8. The method of claim 1, wherein the pulse generator operates to provide a pulse at from about 50 to about 3500 Hz.

9. The method of claim 8, wherein the pulse lasts for from about 1 to about 500 ns.

10. The method of claim 1, wherein the device comprises an apparatus for inductive impedance matching.

11. The method of claim 1, wherein the apparatus for controlling the size of the plasma gap of the device adjusts the plasma gap from about 0.5 to about 5 mm.

12. The method of claim 1, wherein the high voltage electrode has an area of from about 0.1 to about 10 cm$^2$.

13. The method of claim 1, wherein the plasma contacts the tissue for from 10 seconds to 30 minutes.

14. A device for applying a non-thermal atmospheric plasma to a tissue of a patient having actinic keratosis, comprising:

a high voltage electrode, an insulating or semiconducting barrier, a power source capable of providing a voltage, and a pulse generator, the device configured to applying a non-thermal, atmospheric pressure plasma over areas of the tissue having actinic keratosis for a length of time effective to give rise to an at least partial amelioration of the keratosis, the device optionally comprising an apparatus for inductive impedance matching, an apparatus for controlling the size of a plasma gap of the device, or both.

15. The device of claim 14, wherein the device is configured to contact the tissue of the patient.

16. The device of claim 14, wherein the device is configured to apply the non-thermal atmospheric plasma at a distance from the tissue of the patient.

17. The device of claim 14, wherein the non-thermal plasma has an average gas temperature that does not exceed about 400 K.

18. The device of claim 14, wherein the insulating or semiconducting barrier comprises a ceramic, organic or inorganic polymer, glass, or other carbide, nitride, or oxide insulator.

19. The device of claim 14, wherein the power source provides power in the range of from about 10 kV to about 60 kV.

20. The device of claim 14, wherein the pulse generator operates to provide a pulse at from about 50 to about 3500 Hz.

\* \* \* \* \*